United States Patent [19]

Stokes

[11] Patent Number: 4,506,680
[45] Date of Patent: Mar. 26, 1985

[54] DRUG DISPENSING BODY IMPLANTABLE LEAD

[75] Inventor: Kenneth B. Stokes, Minneapolis, Minn.

[73] Assignee: Medtronic, Inc., Minneapolis, Minn.

[21] Appl. No.: 476,436

[22] Filed: Mar. 17, 1983

[51] Int. Cl.$^3$ .............................................. A61N 1/04
[52] U.S. Cl. ................................ 128/786; 128/419 P; 604/891; 604/892
[58] Field of Search ................................ 128/784–786, 128/419 P; 604/285, 890–892

[56] References Cited

U.S. PATENT DOCUMENTS

| 4,101,984 | 7/1978 | MacGregor | 3/1.5 |
| 4,350,271 | 9/1982 | Eckenhoff | 604/892 |
| 4,360,031 | 11/1982 | White | 128/786 |

FOREIGN PATENT DOCUMENTS 0047013  3/1982  European Pat. Off. ............ 128/786

*Primary Examiner*—Lee S. Cohen
*Attorney, Agent, or Firm*—Reed A. Duthler; Joseph F. Breimayer; John L. Rooney

[57] ABSTRACT

A body implantable lead for the delivery of stimulation energy to a desired body site including a drug dispenser carried by the lead which retains a drug to be dispensed while allowing the dispensing of that drug at least adjacent the desired body stimulation site. The drug may be one which is intended to counter thrombus formation, fibrosis, inflammation or arrhythmias, or any combination thereof, or to accomplish any other localized purpose. The drug is retained in a cavity within the lead, with an agency controlling dispensing of the drug. In a preferred embodiment, the drug is compounded into a solid material which is retained within a tip electrode while being exposed to body fluids through a porous elution path. The drug may also be retained on and diffused from a porous surface of the electrode, adjacent to the elution path. Preferably, the drug is compounded within a polymer carrier, mounted within the cavity in the electrode.

7 Claims, 3 Drawing Figures

U.S. Patent  Mar. 26, 1985  Sheet 1 of 2  4,506,680
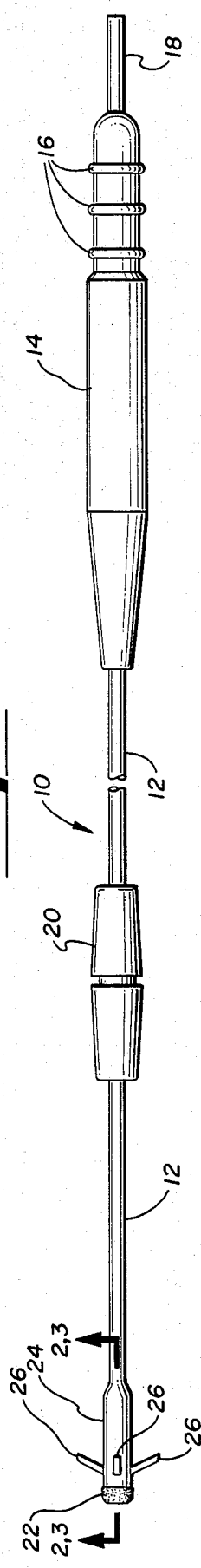
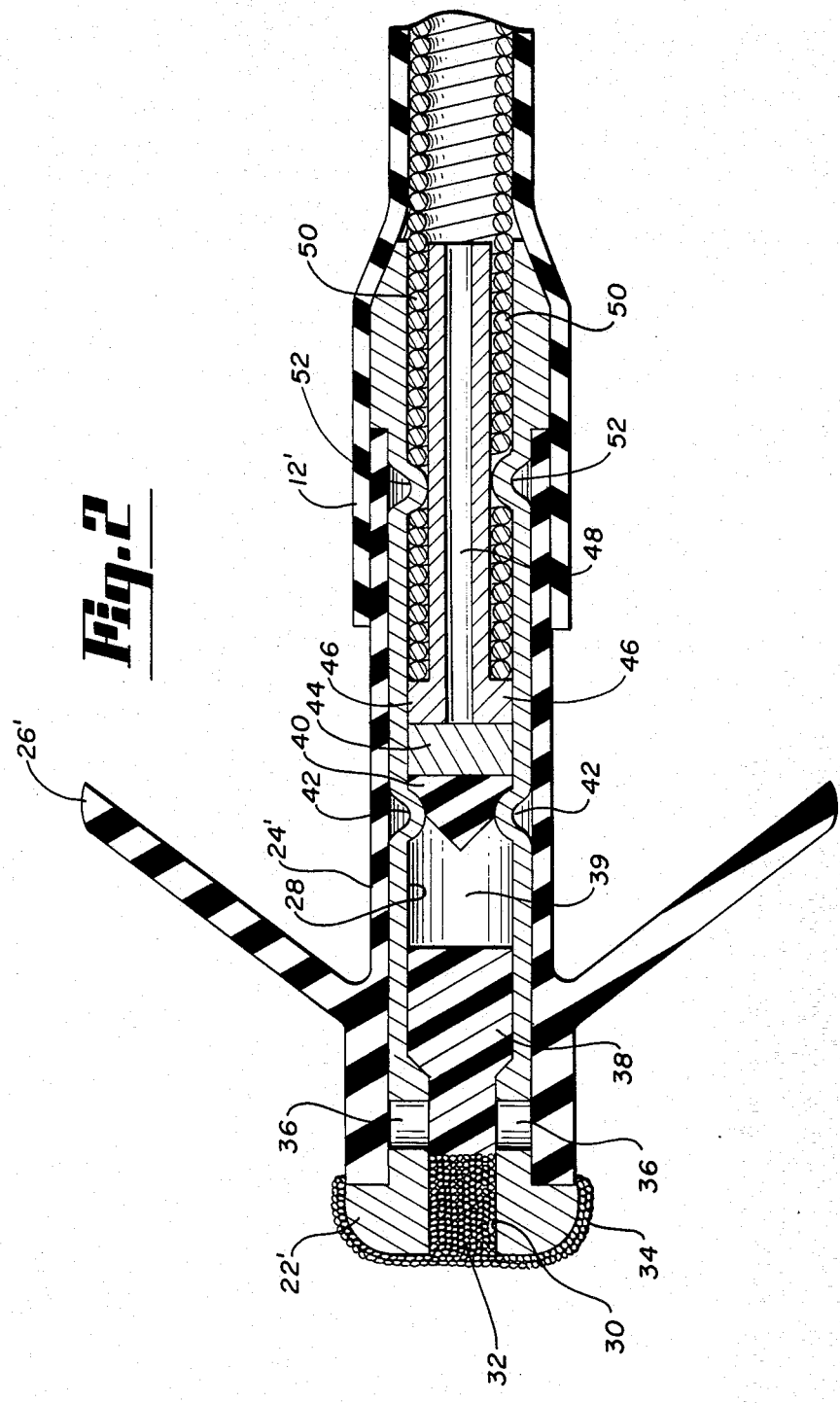

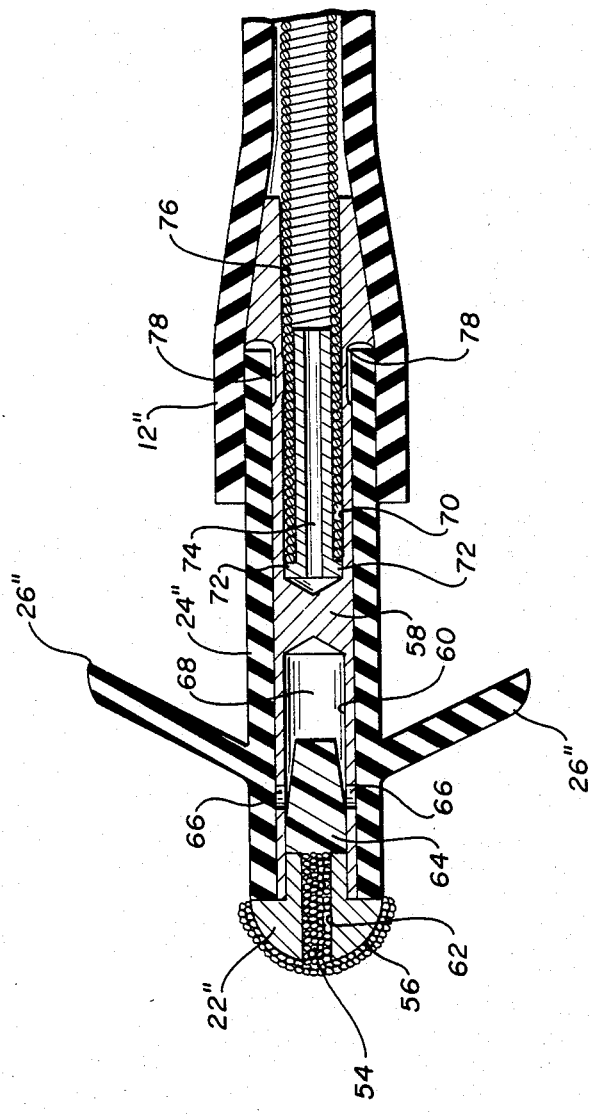

DRUG DISPENSING BODY IMPLANTABLE LEAD

BACKGROUND OF THE INVENTION

1. Field of the Invention

This invention pertains to electrical stimulation leads in general, and to cardiac pacing leads in particular.

2. State of the Prior Art

Electrical stimulation of the body for medical purposes is well known in the prior art. An example of a device for this purpose is the well-known cardiac pacemaker. In the pacemaker context, as well as other body stimulation contexts, the stimulation is delivered to the desired body site by an electrode carrying lead.

Interactions between the lead and body can vitiate the desired effects of the stimulation. For example, material reactions may encourage fibrosis. In the pacemaking context, fibrosis is believed to be a major factor in the increase in chronic stimulation threshold that is usually experienced. Also, mechanical trauma may result in inflamation of the tissue to be stimulated. Such inflamation may alter the response of the tissue to the stimulation energy, both acutely and chronically.

Other interactions between the lead and body, while not directly affecting the response of the tissue to the stimulation energy, can result in the occurrence of undesirable events. In some circumstances where electrical body stimulation is indicated, the body portion to be stimulated is irritable. The placement of a lead may compound this irritability. For example, the placement of a pacemaking lead may induce a cardiac arrhythmia. The presence of the lead may also promote thrombus formation.

The interactions noted above have long been recognized and efforts made to ameliorate their consequences. For example, the lead may be configured to reduce mechanical trauma and the response of irritable tissue during lead placement. Materials may be selected for the lead body and electrodes to minimize fibrosis. However, lead configuration must take into account other factors such as the efficiency of the delivery of the stimulation energy, the ease of lead placement, maintenance of the desired electrode position and reliability of the lead over extended periods of time. An accommodation of these interests has resulted in leads whose configuration necessarily results in undesirable interactions between the lead and body.

It is known that thrombus formation may also be countered by the administration of suitable drugs. It is also known that a systemic treatment with steroids results in acute reduction in the stimulation threshold level. In particular, systemic use of glucocorticosteroids has been used to treat chronic exit block, a condition in which the stimulation threshold rises above the output level of the implanted pacemaker. However, long term systemic use of such steroids often produces undesirable side effects.

SUMMARY OF THE INVENTION

The present invention provides a body implantable lead for the delivery of stimulation energy to a desired body site. A drug dispenser carried by the lead includes a member for retaining the drug to be dispensed while allowing a dispensing of that drug at the desired body stimulation site. The drug may be one intended to counter thrombus formation, fibrosis, inflamation, or arrhythmias, or any combination thereof, or to accomplish any desirable localized purpose. In a preferred embodiment as a cardiac pacing lead, the drug may be the sodium salt of dexamethansone phosphate, a glucocorticosteroid which, when dispensed by a lead according to the present invention, results in a chronic reduction of pacing and sensing thresholds. Most preferably, the lead carries a tip electrode at its distal end with the drug being dispensed through a porous, sintered elution path within the electrode. In some embodiments, it is desirable to additionally apply the drug to a porous portion of the tip electrode, adjacent the exit point of the elution path.

DESCRIPTION OF THE INVENTION

Brief Description of the Drawings

FIG. 1 illustrates a plan view of a body implantable lead constructed in accordance with the present invention, FIG. 2 illustrates a side sectional view of one preferred embodiment of the proximal portion of the lead of FIG. 1.

FIG. 3 illustrates a side sectional view of a second preferred embodiment of the proximal portion of the lead of FIG. 1.

DETAILED DESCRIPTION OF THE DRAWINGS

FIG. 1 illustrates a plan view of a lead constructed in accordance with the present invention. The lead includes an elongated lead body 10 covered by an insulative sheath 12. Insulative sheath 12 may be fabricaed of silicone rubber or polyurethane. At the proximal end of the lead, is connector assembly 14 which is adapted to couple the lead to an implantable pacemaker. Connector assembly 14 is provided with three sealing rings 16 and with a connector pin 18, all of a type known to the art. Surrounding the lead body 10 is anchoring sleeve 20 which serves to anchor and seal the lead at its insertion site. Anchoring sleeve 20 may conveniently be fabricated of silicone rubber. Connector assembly 14 may be fabricated of silicone rubber or polyurethane. Connector pin 18 may be fabricated of stainless steel.

At the proximal end of the lead of FIG. 1 is mounted tip electrode 22. Immediately proximal to tip electrode 22 is distal insulating sheath 24 which bears four tines 26. Tines 26 are of known design and form no part of the present invention, aside from forming a portion of the disclosed preferred embodiment thereof. Sheath 24 may be fabricated of silicone rubber or polyurethane.

FIG. 2 is a side sectional view of one preferred embodiment of the proximal portion of the lead of FIG. 1. Electrode 22' corresponds to electrode 22 of the lead shown in FIG. 1. Distal insulating sheath 24', tines 26' and insulative sheath 12' similarly correspond to the structures labeled 24, 26 and 12 shown in FIG. 1. In this view, it can be seen that electrode 22' extends proximally within distal insulative sheath 24' and within insulative sheath 12'. Electrode 22' is provided with a central bore 28. Central bore 28 is narrowed at its most distal portion to form elution bore 30. Within elution bore 30 is porous elution path 32. Covering the outer surface of electrode 22' is porous coating 34. Electrode 22', along with porous elution path 32 and porous coating 34 are preferably fabricated of any conductive, inert metal such as platinum or titanium. However, electrode structures fabricated using carbon or ceramic elements are believed within the scope of the invention. Porous elution path 32 and porous coating 34 are sintered metal structures, and may be manufactured using the technique set forth in U.S. Pat. No. 3,855,638, issued to Pillar, and incorporated herein in its entirety. By varying the porousity of the elution path 32, elution rate may be controlled.

Proximal to porous elution path 32 are vent holes 36, formed as a cross bore, perpendicular to bore 28 of electrode 22'. Vent holes 36 serve two functions. First, vent holes 36 allow the proper placement of silicone plug 38 to be determined during assembly of the lead. In addition, it is believed that vent holes 36 provide an exit path for air displaced as a result of the swelling of plug 38, mounted within bore 28. Plug 38 is constructed of a polymer impregnated with the desired drug. It is desirable that the drug be water soluble so that it efficiently elutes into body fluid. In a preferred embodiment, plug 38 is silicone rubber impregnated with the sodium salt of dexamethasone phosphate. The water soluble forms of other glucocorticosteroids, such as prednisone, are also believed to be appropriate for use in the present invention. Plug 38 may be fabricated by mixing the drug with silicone rubber medical adhesive, and allowing the mixture to cure.

Incorporation of dexamethasone sodium phosphate renders the silicone rubber of plug 38 swellable by body fluids. That portion of bore 28 not filled by silicone plug 38 provides an expansion space 39 for expansion of plug 38 proximally while porous elution path 32 prevents expansion of plug 38 through elution bore 30. Sealing bore 28 proximal to expansion space 39 is sealing washer 40, which is retained by means of crimps 42 and metal disk 44. Proximal to metal disk 44 is swaging pin 46, which is provided with a central bore 48, into which a stylet may be inserted. Coiled conductor 50 is frictionally attached to electrode 22 by means of crimps 52 which hold coiled conductor 50 firmly between swaging pin 52 and electrode 22'. Coiled conductor 50 extends through lead body 10 to the proximal end of the lead, and is coupled to connector pin 18 (FIG. 1). Metal disk 44, and swaging pin 46 may be fabricated of any inert, non-corroding conductive metal. Coiled conductor 50 is preferably fabricated of MP35 alloy or of drawn-brazed-strand wire.

In use, body fluid enters silicone plug 38 via porous elution path 32. The body fluid causes silicone plug 38 to swell, expanding into the expansion space 39. The drug, being water soluble, elutes out of the lead through porous elution path 32. Experimental use of the lead has indicated that for longer porous elution paths, for example, 0.075" or more, it is desirable to also wet porous coating 34 with the drug, prior to introduction of the lead into the heart. This prewetting of the electrode with the drug appears to encourage flow of the drug out of silicone plug 38, as well as providing a higher acute concentration of the drug. Prewetting of electrode 22' may be accomplished by dipping it into a solution of the drug in water and alcohol.

FIG. 3 illustrates a side sectional view of a second preferred embodiment of the distal portion of a lead according to the present invention. As in FIG. 2 above, elements labeled 22", 24", 26", and 12" correspond to structures 22, 24, 26, and 12 of FIG. 1. Like the lead of FIG. 2, the lead of FIG. 3 employs a porous elution path 54 and a porous coating 56. Electrode 22" is coupled to inner electrode member 58. Inner electrode member 58 is provided with a first bore 60 which is coaxial to and exposed to elution bore 62 of electrode 22". Mounted within bore 60 is silicone plug 64, which corresponds to silicone plug 38 of FIG. 2 above. Inner electrode element 58 is provided with vents 66, open to bore 60. These vents serve the same purpose as vents 36 shown in FIG. 2. As in the lead of FIG. 2 above, an expansion space 68 is provided into which silicone plug 64 may expand as it swells. Because inner electrode element 58 is machined out of a solid piece of metal, there is no need for the sealing washer and metal disk of the lead of FIG. 2. Inner electrode element 58 has a second bore 70, in which swaging pin 72 is mounted. Swaging pin 72 is provided with a central bore 74 in which a stylet may be inserted. Coiled conductor 76 is frictionally coupled to inner electrode element 58 by means of crimps 78 which hold coiled conductor 76 firmly between swaging pin 72 and inner electrode element 58. Coiled conductor 76 extends proximally within insulative sheath 12 to connector pin 18 (FIG. 1). This lead functions in the same manner as the lead of FIG. 2.

By constructing a lead according to the above invention, several advantages may be realized. First, the amount of energy required to stimulate the heart as compared with electrodes of similar size, either with or without a porous coating is substantially reduced. This reduction in stimulation threshold allows for a corresponding reduction in the required energy output of the pacemaker attached to the lead, extending its battery life.

Second, a lead according to the present invention also facilitates detection of electrical heart activity. It is well known to the art that smaller surface area electrodes present a higher source impedance, which distorts and attenuates the sensed electrical activity of the heart. Electrodes according to the present invention, however, present a source impedance lowered substantially as compared to similarly sized electrodes without a porous surface. In addition, the present design results in a significantly lower pacing impedance than similarly sized electrodes either with or without a porous surface. These two factors allow the use of very small surface area electrodes, 4.5 mm$^2$ or less, to raise pacing impedance to a level more typical of prior art electrodes without sacrificing the ability to sense heart activity. The smaller electrode size permittted by the present invention results in higher current density during stimulation pulses, providing more efficient stimulation of the heart tissue with lower current drain from the implanted pacemaker.

An additional benefit of the present invention flows from the localized nature of the drug treatment. It is well known that various systemic drugs affect the electrical characteristics of the heart, and thus may effect the functioning of an implanted pacemaker. The present invention allows for use of drugs to counter such effects, without interfering with the systemic drug. The localized application of the drug of the present invention also avoids undesirable side effects which systemic use of the drug might produce.

Other and further embodiments of the invention are readily apparent from the above description of the invention, and these embodiments are within the scope of the invention disclosed herein.

What is claimed is:

1. A cardiac pacing lead comprising:
   an elongated electrical conductor having a proximal and a distal end;
   an insulative sheath covering said electrical conductor;

an electrical connector coupled to the proximal end of said electrical conductor;

an electrode having an exterior surface and coupled to the distal end of said electrical conductor; and drug dispensing means for dispensing a drug at said electrode having a cavity for retaining said drug and an elution bore open to said cavity and to the exterior surface of said electrode, said drug dispensing means further comprising a plug of a swellable polymer located within said cavity containing a water soluble drug, said plug having a volume smaller than the volume of the cavity of said drug dispensing means, the elution bore of said drug dispensing means having means for preventing expansion of said plug through said elution bore while permitting elution of the drug through said elution bore.

2. A lead according to claim 1 wherein said means for preventing expansion comprises a porous structure, located within the elution bore of drug dispensing means.

3. A lead according to claim 2 wherein said porous structure comprises sintered metal particles, spanning the elution bore of said drug dispensing means.

4. A lead according to claim 3 wherein said drug is the sodium salt of dexamethasone phosphate and wherein said polymer is silicone rubber.

5. A lead according to claim 1 wherein said drug dispensing means further comprises vent means for release of air displaced by the expansion of said plug within the cavity of said drug dispensing means.

6. A cardiac pacing lead comprising:

an elongated electrical conductor having a proximal and a distal end;

an insulative sheath covering said conductor;

an electrical connector coupled to the proximal end of said conductor;

an electrode having an exterior surface and coupled to the distal end of said conductor; and drug dispensing means for dispensing a drug at said electrode, having a cavity for retaining said drug and a bore open to said cavity and to the exterior surface of said electrode, said bore enclosing porous means for controlling the rate of elution of said drug through said bore, said electrode having porous means for retaining said drug located on the exterior surface of said electrode adjacent the bore of said drug dispensing means.

7. A lead according to claim 6 wherein said means for controlling elution rate and said means for retaining said drug are porous structures of sintered metal particles.

* * * * *